(12) United States Patent
Stevenson et al.

(10) Patent No.: US 6,882,248 B2
(45) Date of Patent: Apr. 19, 2005

(54) EMI FILTERED CONNECTORS USING INTERNALLY GROUNDED FEEDTHROUGH CAPACITORS

(75) Inventors: Robert A. Stevenson, Canyon Country, CA (US); Richard L. Brendel, Carson City, NV (US)

(73) Assignee: Greatbatch-Sierra, Inc., Carson City, CA (US)

( * ) Notice: Subject to any disclaimer, the term of this patent is extended or adjusted under 35 U.S.C. 154(b) by 56 days.

(21) Appl. No.: 10/354,818

(22) Filed: Jan. 29, 2003

(65) Prior Publication Data

US 2003/0139096 A1 Jul. 24, 2003

Related U.S. Application Data

(63) Continuation-in-part of application No. 09/657,123, filed on Sep. 7, 2000, now Pat. No. 6,529,103.
(60) Provisional application No. 60/354,083, filed on Jan. 30, 2002.

(51) Int. Cl.[7] .................................................. H03H 7/01
(52) U.S. Cl. ........................ 333/182; 333/185; 361/302
(58) Field of Search ................................ 333/182, 185; 361/302

(56) References Cited

U.S. PATENT DOCUMENTS

| | | |
|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,424,551 A | 1/1984 | Stevenson et al. |
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,670,063 A | 9/1997 | Hegner et al. |
| 5,751,539 A | 5/1998 | Stevenson et al. |
| 5,825,608 A | 10/1998 | Duva et al. |
| 5,905,627 A | 5/1999 | Brendel et al. |
| 5,959,829 A | 9/1999 | Stevenson et al. |
| 5,973,906 A | 10/1999 | Stevenson et al. |
| 6,008,980 A | 12/1999 | Stevenson et al. |
| 6,566,978 B1 * | 5/2003 | Stevenson et al. .......... 333/182 |

* cited by examiner

Primary Examiner—Robert Pascal
Assistant Examiner—Dean Takaoka
(74) Attorney, Agent, or Firm—Kelly Lowry & Kelley, LLP

(57) ABSTRACT

An EMI filtered connector includes a plurality of conductive terminal pins, a grounded conductive connector housing through which the terminal pins pass in non-conductive relation, and an array of feedthrough filter capacitors. Each of the feedthrough filtered capacitors has a distinct first set of electrode plates, a non-distinct second set of electrode plates, and a first passageway through which a respective terminal pin extends in conductive relation with the first set of electrode plates. At least one ground lead is conductively coupled to the conductive connector housing and extends into a second passageway through the array of feedthrough filter capacitors in conductive relation with the second set of electrode plates. An insulator is disposed in or adjacent to the connector for mounting the conductive terminal pins for passage through the conductive connector with the conductive terminal pins and the connector in non-conductive relation. The outer peripheral surface of the array of feedthrough filter capacitors is non-conductive.

25 Claims, 15 Drawing Sheets

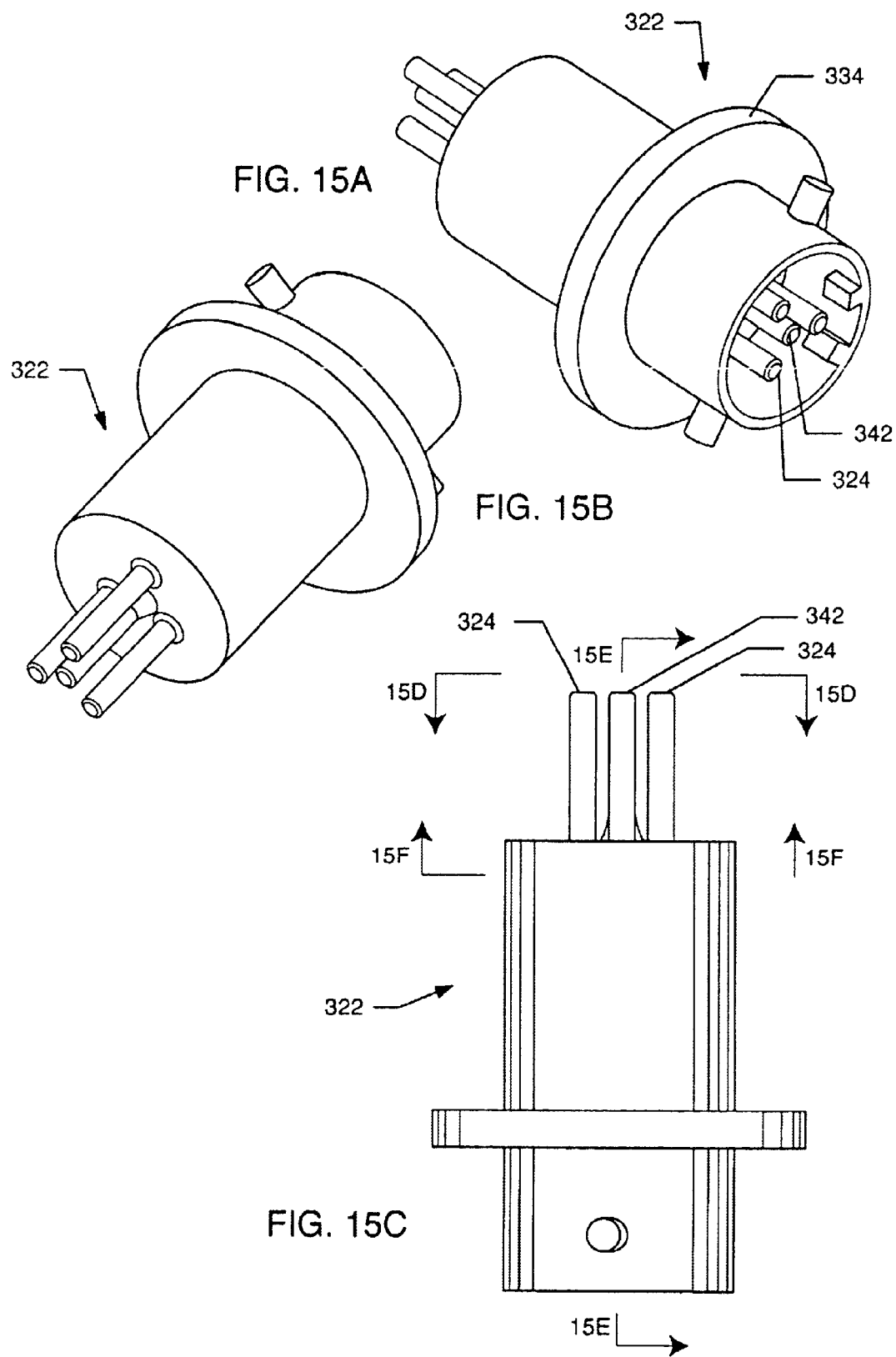

EMI FILTERED CONNECTORS USING INTERNALLY GROUNDED FEEDTHROUGH CAPACITORS

RELATED APPLICATIONS

This application claims priority from Provisional Application No. 60/354,083, filed Jan. 30, 2002. This application is also a continuation-in-part application of U.S. patent application Ser. No. 09/657,123, filed Sep. 7, 2000 now U.S. Pat. No. 6,529,103, entitled INTERNALLY GROUNDED FEEDTHROUGH FILTER CAPACITOR WITH IMPROVED GROUND PLANE DESIGN FOR HUMAN IMPLANT AND OTHER APPLICATIONS. The contents of these prior applications are incorporated herein.

BACKGROUND OF THE INVENTION

This invention relates generally to EMI filtered connectors. More specifically, the present invention relates to EMI filtered connectors which utilize one or more internally grounded feedthrough capacitors.

Internally grounded ceramic feedthrough filter capacitors greatly improve the reliability and reduce cost of EMI filters for medical implant terminals. Exemplary internally grounded feedthrough capacitors are shown and described in U.S. Pat. No. 5,905,627 entitled INTERNALLY GROUNDED FEEDTHROUGH FILTER CAPACITOR, the contents of which are incorporated herein.

Ceramic feedthrough capacitors are used in a wide range of electronic circuit applications as EMI filters. Feedthrough capacitors are unique in that they provide effective EMI filtering over a very broad frequency range. For example, this can be from a few Kilohertz to tens of Gigahertz. The mounting or installation of feedthrough capacitors in a typical electronic circuit is always problematic. For one thing, in order to provide proper shielding and attenuation the EMI filter must be installed as a continuous part of the overall EMI shield. This overall EMI shield is usually metallic. Because of the metallic nature of most EMI shields, the installation of a relatively brittle barium titinate-based ceramic capacitor is inherently problematic. This is due to mismatches in thermal coefficient of expansion and resulting mechanical stresses, which can fracture the relatively brittle monolithic ceramic capacitor and lead to either immediate or latent electrical failures. The internally grounded capacitor described in U.S. Pat. No. 5,905,627 was designed to overcome these difficulties.

FIG. 1 illustrates filtered connectors 20a–20l that are typically used in the military, aerospace, medical, telecommunication and other industries. In an EMI filtered connector, such as those typically used in aerospace, military, telecommunications and medical applications, it is very difficult to install the feedthrough capacitor to the connector housing or back shell without causing excessive mechanical stress to the ceramic capacitor. A number of unique mounting schemes are described in the prior art, which are designs that mechanically isolate the feedthrough capacitor while at the same time provide the proper low impedance ground connection and RF shielding properties. This is important because of the mechanical stresses that are induced in a filtered connector. It is problematic to install a relatively brittle ceramic feedthrough capacitor in a filtered connector because of the resulting mismatch in thermal coefficient of expansion of the surrounding materials, and also the significant axial and radial stresses that occur during connector mating.

By definition, connectors come in female and male versions to be mated during cable attach. The EMI filtering is typically done in either the female or the male portion, but usually not both. During the insertion or mating of the connector halves, significant mechanical forces are exerted which can be transmitted to the feedthrough capacitor.

As described in U.S. Pat. No. 5,905,627, the capacitor ground electrode plate is internally attached to one or more lead wires, which can pass all the way through the device or to one or more grounded studs. In the '627 patent, these capacitors were shown uniquely mounted to a variety of implantable medical hermetic terminals such as those used in cardiac pacemakers, implantable defibrillators and the like. By way of example, U.S. Pat. No. 5,905,627 illustrates a rectangular feedthrough capacitor with an internally grounded electrode, which is also shown as FIGS. 2 through 6 herein.

More particularly, an internally grounded feedthrough filter capacitor assembly is generally designated in FIG. 6 by the reference number 22. The feedthrough filter capacitor assembly 22 comprises, generally, at least one conductive terminal pin 24 and a conductive ferrule 26 through which the terminal pin passes in non-conductive relation. An insulator 28 supports each conductive terminal pin 24 from the conductive ferrule 26 in electrically insulated relation, and the assembly of the terminal pins, the conductive ferrule and the insulators comprises a terminal pin sub-assembly 30. The feedthrough filter capacitor assembly 22 further includes a feedthrough filter capacitor 32 that has first and second sets of electrode plates 34 and 36. A first passageway 38 is provided through the feedthrough filter capacitor 32 through which the terminal pin 24 extends in conductive relation with the first set of electrode plates 34. The feedthrough filter capacitor 32 further includes a second passageway 40 into which a ground lead 42 extends. The ground lead 42 is conductively coupled to the second set of electrode plates 36 and the conductive ferrule 26. Typically, the conductive ferrule 26 is conductively mounted to a conductive substrate 44 that may comprise, for example, the housing for an implantable medical device.

The internally grounded feedthrough filter capacitor assembly 22 eliminates the need for external conductive connections between the capacitor and a ground by connecting the internal ground plates to a ground pin, tubelet, or similar ground lead structure. This is a particularly convenient and cost effective approach for certain implantable cardioverter defibrillators (ICDs) that already employ a grounded terminal pin in order to use the titanium housing of the implanted ICD as one of the cardiac electrodes. As there is no external electrical connection, the need for external capacitor metalization around the capacitor perimeter or outside diameter has been eliminated. This not only reduces expensive metallization firing or plating operations, but also eliminates the joining of materials which are not perfectly matched in thermal coefficient of expansion.

The feedthrough filter capacitor 32 comprises a monolithic, ceramic internally grounded bipolar feedthrough filter capacitor having three passageways extending therethrough. The outer two passageways are configured to receive therethrough respective conductive terminal pins 24, and the internal diameter of the first passageways 38 are metallized to form a conductive link between the first sets of electrode plates 34. As is well understood in the art, the first sets of electrode plates 34 are typically silk-screened onto ceramic plates forming the feedthrough filter capacitor 32. These plates 34 are surrounded by an insulative ceramic material that need not metallized on its exterior surfaces.

Similarly, a second set of electrode plates 36 is provided within the feedthrough filter capacitor 32. The inner diameter of the central or second passageway 40 through the feedthrough filter capacitor 32 is also metallized to conductively connect the second set of electrode plates 36 which comprise the ground plane of the feedthrough filter capacitor 32. The second passageway 40 is configured to receive therethrough the ground lead 42 which, in this particular embodiment, comprises a ground pin.

With reference to FIG. 5, the terminal pin subassembly 30 comprises a plate-like conductive ferrule 26 having three apertures therethrough that correspond to the three passageways through the feedthrough filter capacitor 32. The conductive terminal pins 24 are supported through the outer apertures by means of an insulator 28 (which also may be hermetic), and the ground pin 42 is supported within the central aperture by a suitable conductor 46 such as a solder, an electrically conductive thermal setting material or welding/brazing.

The feedthrough filter capacitor 32 is placed adjacent to the non-body fluid side of the conductive ferrule 26 and a conductive attachment is effected between the metallized inner diameter of the first and second passageways 38 and 40 through the feedthrough filter capacitor 32 and the respective terminal pins 24 and ground lead 42. As was the case described above in connection with the attachment of the ground lead 42 to the conductive ferrule 26, the conductive connection 48 between the terminal pins 24 and the ground lead 42 with the feedthrough filter capacitor 32 may be effected by any suitable means such as a solder or an electrically conductive thermal setting material or brazing. The result is the feedthrough filter capacitor assembly 22 illustrated in FIG. 6 which may then be attached to the conductive substrate 44.

EMI filtered connectors are typically manufactured using monolithic ceramic capacitor arrays 50a and 50b. Examples of these multi-hole capacitor arrays are shown in FIG. 7. Planar arrays can vary in the number of feedthrough holes from one all the way up to several hundred in some cases. In the planar arrays 50a and 50b shown in FIG. 7, both the inside diameter of the feedthrough holes 52 and the entire outside perimeter 54 are metallized. The purpose of the metallization is to connect the electrode plates in parallel and to provide a surface for electrical attachment to the capacitor. The metallization usually consists of a fired-on silver loaded glass frit, plating, or the like (sometimes gold terminations are used). The general material used for the dielectric is barium titinate. Accordingly, these devices, when fired, are very brittle (and mechanically weak). In an EMI filtered connector, the brittle ceramic capacitor does not match the thermal coefficient of expansion of the surrounding connector metallic material (such as the connector housing or back shell). Because of this, mechanical stresses are introduced during capacitor installation, mechanical connector mating and during temperature cycling.

FIG. 8 is a cross-sectional view of a typical filtered connector 56 in a π filter configuration. As can be seen the two ceramic discoidal capacitors 58 are directly attached to the inside diameter of the connector. This results in an area of high stress concentration, which can lead to fractures of the monolithic ceramic capacitor. These fractures can result in either immediate or latent electrical failure. A number of manufacturers of filtered connectors have gone to great lengths to mechanically isolate the ceramic feedthrough capacitor. FIG. 9 is an illustration of such a system, which shows spring contact fingers 60, 62 which isolate the capacitors 58 (disposed on either side of an intermediate ferrite inductor 64) mechanically, both for the ground connections to the connector 56 and the connection between the lead wire 66 and the capacitor inside diameter. This allows the capacitors 58 to structurally float thereby making them much less sensitive to damage during connector insertion or during thermal cycling.

FIG. 10 is a connector manufactured by Amphenol utilizing beryllium copper contact resistance clips 68, which provide the ground spring as previously described in FIG. 9. FIG. 10 also illustrates that a beryllium copper EMI grounding spring 70 has been used at the inside diameter contact of the ceramic capacitor. This assembly has been very successful in the industry; however, it is quite complicated and expensive to manufacture. FIG. 10 further illustrates a machine aluminum alloy shell 72, a stainless steel socket hood 74, front removable machine copper alloy contacts 76, a silicone rubber interfacial seal 78, a high temperature dielectric insert 80, a monolithic planar capacitor array 82, sealing and stress isolating elastomeric gaskets 84, a fixed rear nation contact 86, and a ferrite inductor 88.

FIG. 11 illustrates yet another prior art Amphenol connector which has utilized grounding springs 68 and 70 in order to isolate the monolithic ceramic capacitor array from the mechanical stresses due to the connector itself. Components illustrated in FIG. 11 that are equivalent to the components of the connector of FIG. 10 show the same reference number.

In summary, FIGS. 8 through 11 illustrate various methods of installing ceramic capacitor arrays inside of a connector back shell or housing. As can be seen, the capacitors as installed in FIG. 8 are subject to damage caused by both mechanical and thermal stresses. Solutions as indicated in FIGS. 9, 10 and 11, are effective; however, they are expensive, complicated and not very volumetrically efficient.

Accordingly, there is a need for novel filter connectors which utilize the internally grounded feedthrough capacitor as described above in a variety of filtered connector applications. Modification of the connector is needed to adapt it to be compatible with the internally grounded capacitors. Such modifications must provide a low impedance electrical connection that will operate to several gigahertz while at the same time mechanically isolating the ceramic capacitor so that excessive mechanical stresses do not result. The present invention fulfills these needs and provides other related advantages.

SUMMARY OF THE INVENTION

The present invention resides in an improved EMI filtered connector which provides the proper degree of both thermal and mechanical isolation of an array of feedthrough filter capacitors from the connector housing and yet at the same time provides a low impedance RF connection so that a high degree of EMI filtering effectiveness is maintained. The EMI filtered connector of the present invention comprises, generally, a plurality of conductive terminal pins, a grounded conductive connector housing through which the terminal pins pass in non-conductive relation, and an array of feedthrough filter capacitors each having a distinct first set of electrode plates, a non-distinct second set of electrode plates, and a first passageway through which a respective terminal pin extends in conductive relation with the first set of electrode plates. As used herein, a distinct set of electrode plates refers to a set of electrode plates which are distinctly separate and associated with a particular capacitor of the feedthrough filter capacitor array. A non-distinct set of electrode plates refers to those plates which are common to two or more of the distinct capacitors in the array of feedthrough filter capacitors. At least one ground lead is conductively coupled to the conductive connector housing, and extends into a second passageway through the array of feedthrough filter capacitors in conductive relation with the second set of electrode plates.

In a preferred form of the invention, the outer peripheral surface of the array of feedthrough filter capacitors is non-conductive. Further, an insulator is disposed in or adjacent to the connector, for mounting the conductive terminal pins for passage through the conductive connector with the conductive terminal pins and the connector is non-conductive relation. The insulator may provide means for hermetically sealing passage of the terminal pins through the connector housing, as well as means for hermetically sealing passage of the ground lead through the connector housing.

The array of feedthrough filter capacitors may be symmetrical about the ground lead or asymmetrical. The ground lead may form a portion of the connector housing. Further, an insulative washer may be disposed between the array of feedthrough filter capacitors and the connector housing.

In one illustrated embodiment, a grounding ring is conductively coupled to the ground lead and to the connector housing. The grounding ring is secured to the ground lead utilizing a conductive washer and a retaining clip. As shown, a plurality of ground leads in conductive relation with the second set of electrode plates are provided, wherein all of the ground leads are conductively coupled to the grounding ring.

A plurality of arrays of feedthrough filter capacitors may be provided within a single grounded conductive connector. In this case, each of the plurality of arrays of feedthrough capacitors may be provided with its own non-distinct second set of electrode plates.

A novel feature of the internally grounded feedthrough capacitor is the elimination of all electrical and mechanical attachments to the outside diameter or the perimeter of the feedthrough capacitor. This allows the filtered capacitor to float on the connector pins thereby eliminating the problems with conventional connectors. The result is a more cost effective and much more reliable filtered connector assembly.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIGS. 15A–15F illustrate a circular quadpolar connector with an internally grounded feedthrough capacitor.

DETAILED DESCRIPTION OF THE PREFERRED EMBODIMENTS

Figure 1:
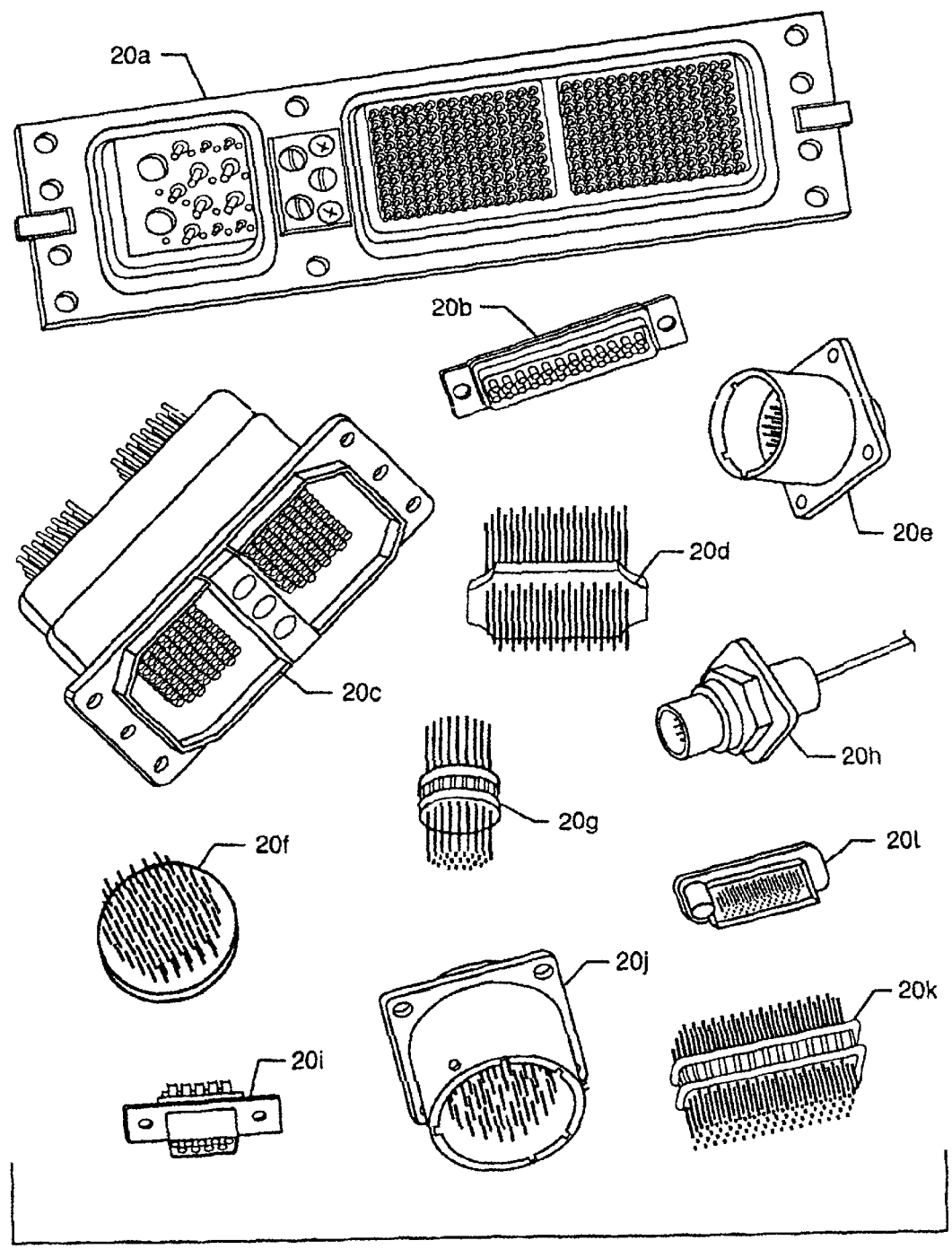
FIG. 1 illustrates prior art filtered connectors that are typically used in the military, aerospace, medical, telecommunication and other industries.
Figure 2:
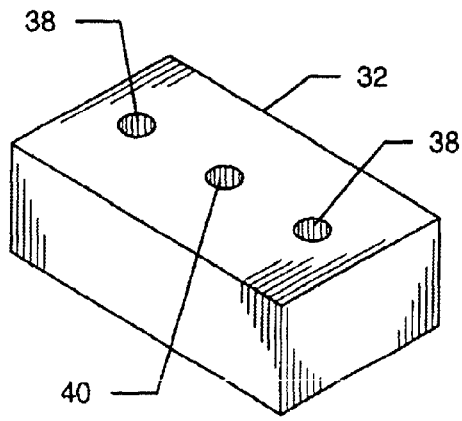
FIG. 2 illustrates a prior art internally grounded feedthrough capacitor in accordance with U.S. Pat. No. 5,905,627.
Figure 3:
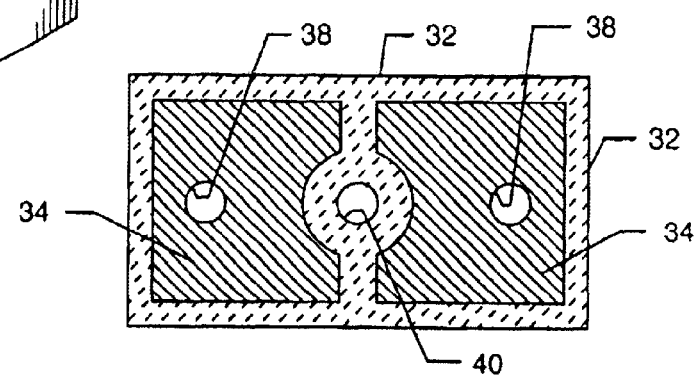
FIG. 3 illustrates the active electrode plate pattern of the capacitor of FIG. 2.
Figure 4:
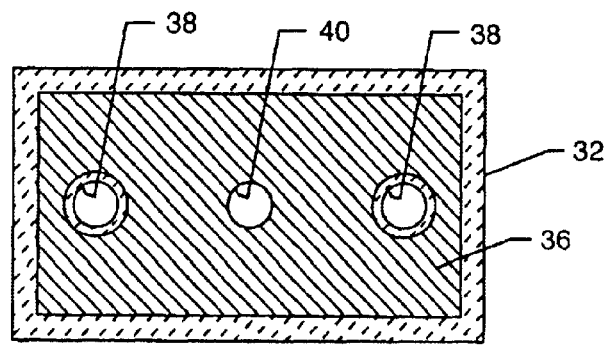
FIG. 4 illustrates the ground electrode plate pattern of the capacitor of FIG. 2.
Figure 5:
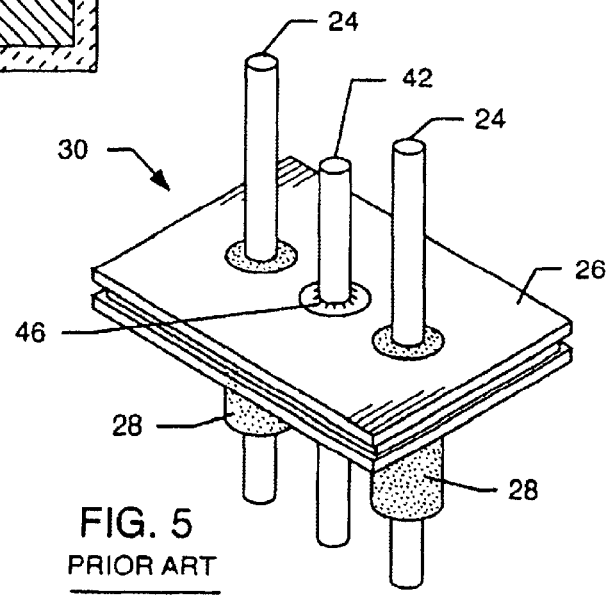
FIG. 5 illustrates a hermetically sealed terminal which includes the capacitor of FIG. 2.
Figure 6:
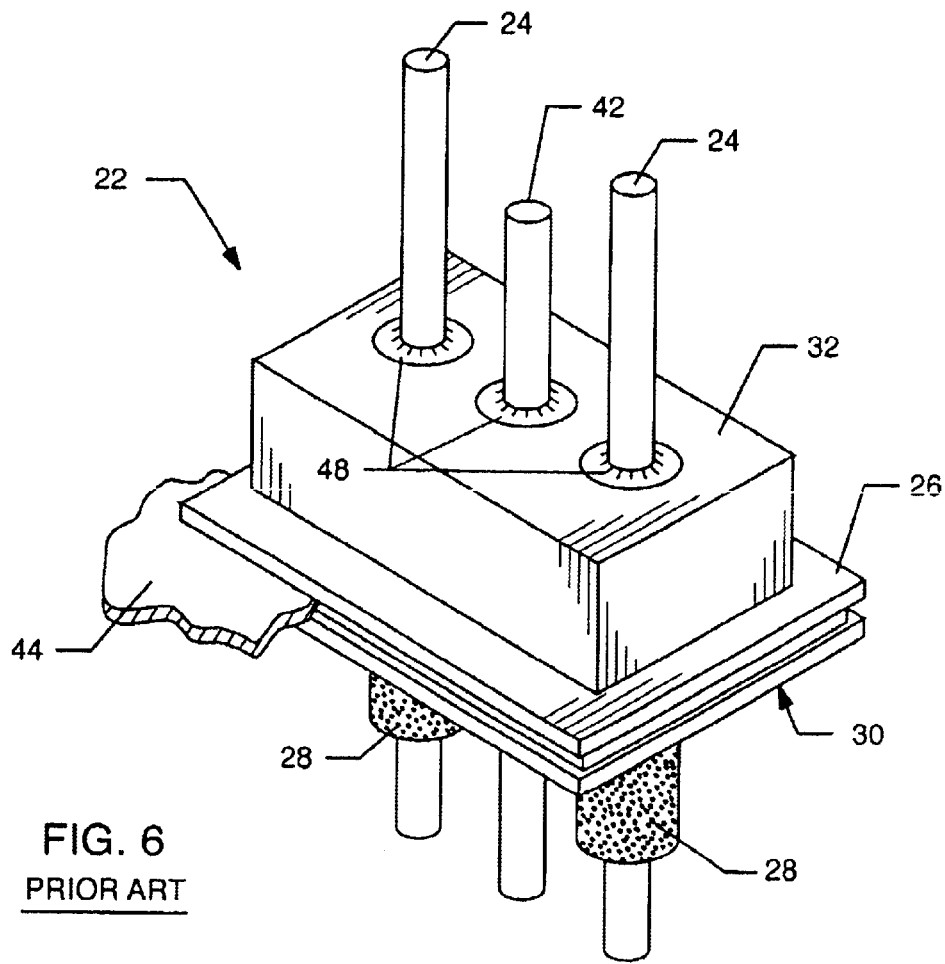
FIG. 6 illustrates the internally grounded capacitor of FIG. 2 mounted to a hermetic seal terminal and housing of an implantable defibrillator.
Figure 7:
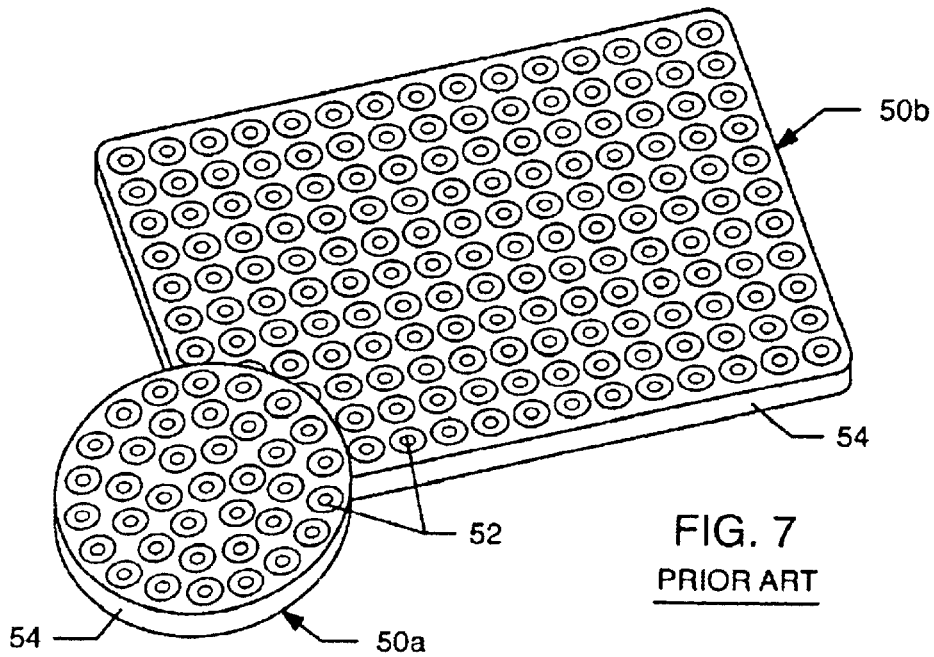
FIG. 7 shows examples of typical prior art multi-hole capacitor arrays.
Figure 8:
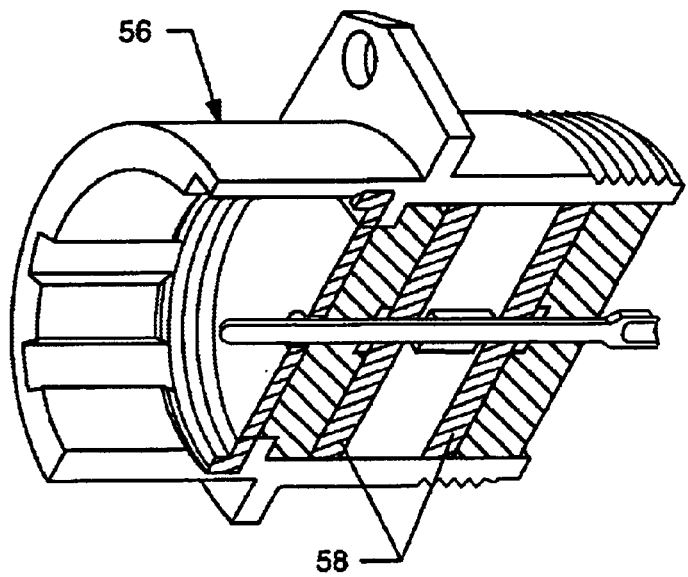
FIG. 8 is a cross-sectional view of a typical prior art filtered connector in a n filter configuration, with direct OD (outer diameter) attach and resultant high mechanical stress to the capacitors.
Figure 9:
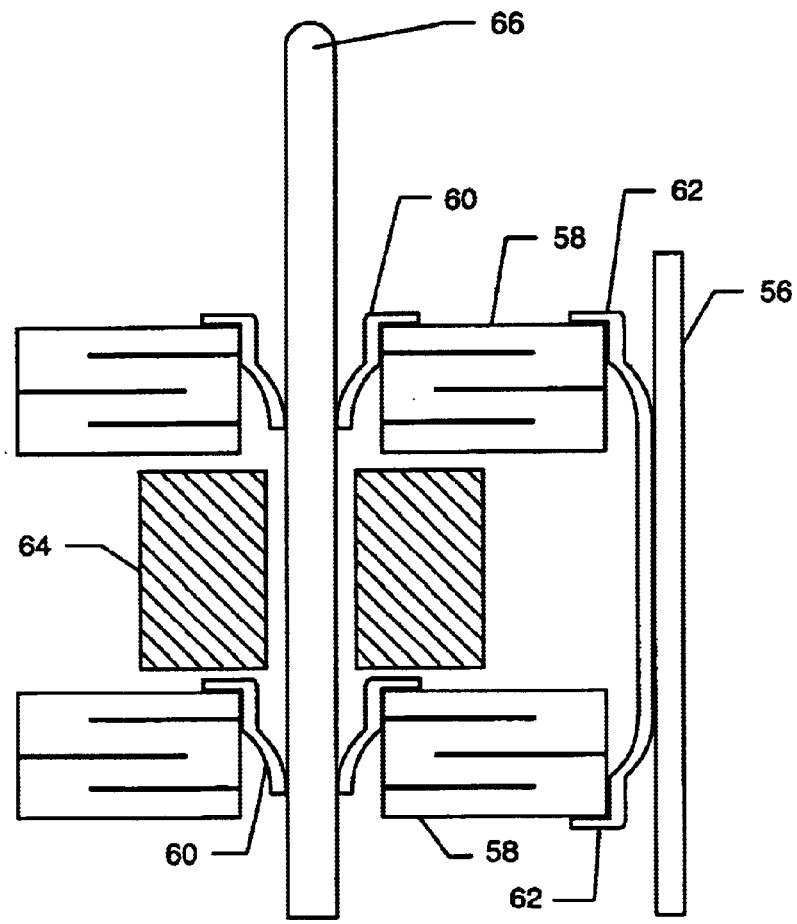
FIG. 9 is a cross-sectional view of a prior art feedthrough capacitor with spring attachments.
Figure 10:
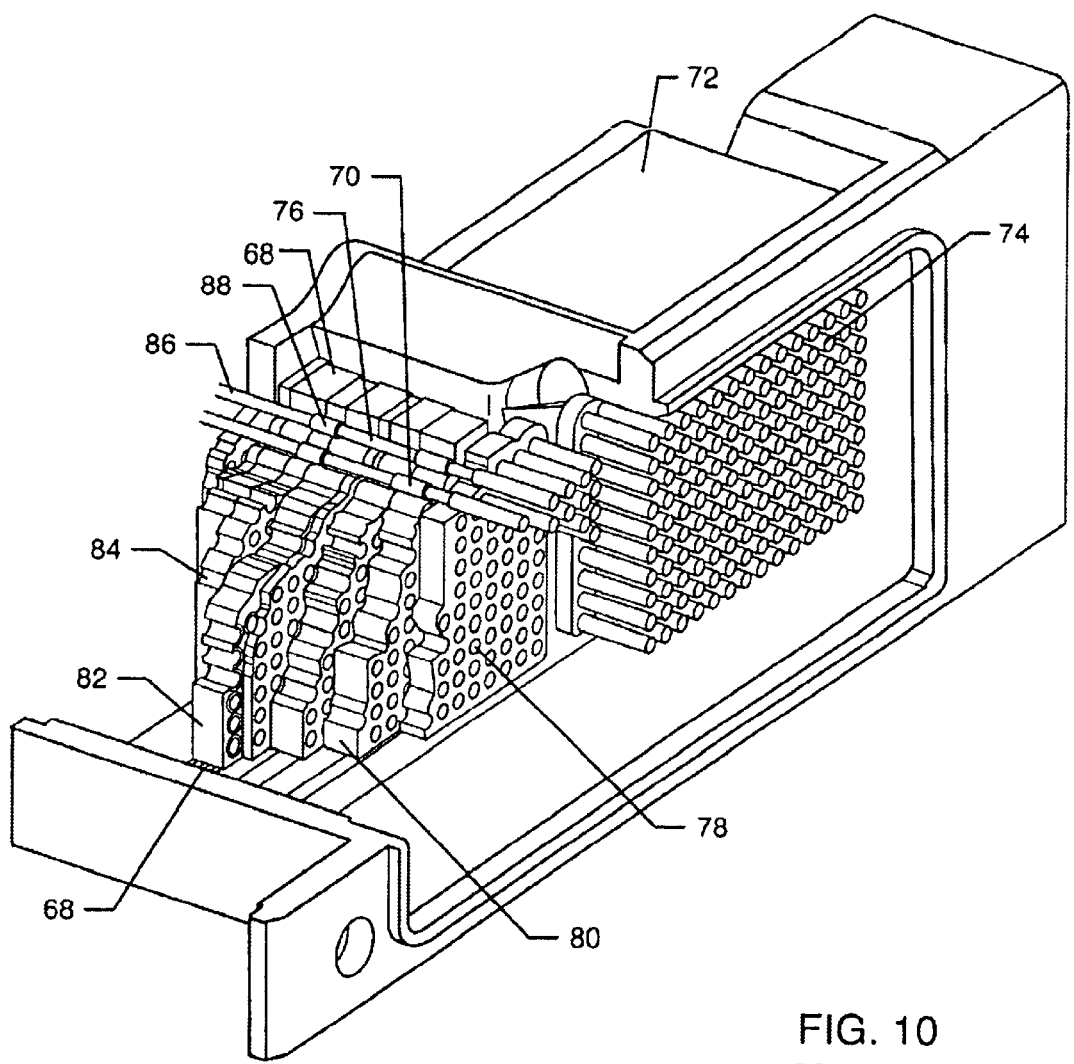
FIG. 10 is a cross-sectional view of a prior art Amphenol filtered connector.
Figure 11:
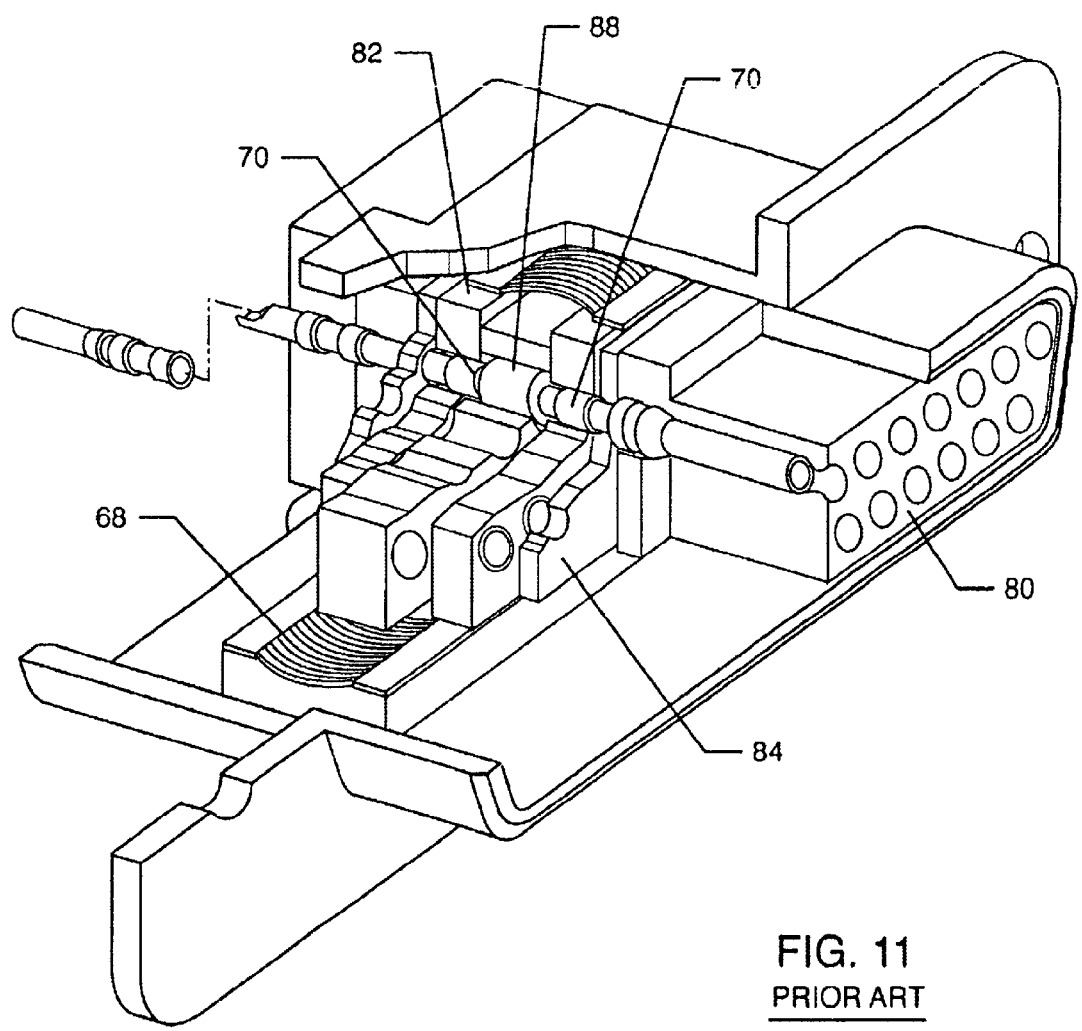
FIG. 11 is a cross-sectional view of a prior art Amphenol filtered connector with EMI grounding springs.

The present invention relates to a method for mounting a monolithic ceramic capacitor to an electronic connector in a manner which provides the proper degree of both thermal and mechanical isolation from the connector housing and yet at the same time provides a low impedance RF connection so that a high degree of EMI filtering effectiveness (attenuation) is maintained. A feature of the present invention is that an internally grounded electrode plate can be grounded at multiple points (not just at its outside diameter or perimeter). This overcomes a serious deficiency in prior art filtered connectors that are physically large. In a large conventional prior art filtered connector, the pins closest to the center are a relatively long distance from the outside diameter or perimeter ground. This creates inductance which tends to reduce the filtering efficiency (attenuation in dB) of these pins. This situation is remedied by the use of a grounded pin near to the center of the array. A multipoint ground attachment assures that the capacitor ground plane will present a very low RF impedance to ground which guarantees that the feedthrough capacitor will operate as a broadband filter with a high level of attenuation. Moreover, use of an internal ground eliminates the outer diameter (OD) termination on the capacitor, and also eliminates of the need for an electrical/mechanical connection between the shielded case or housing and the capacitor OD (or perimeter in the case of rectangular feedthrough).

In the following description of the preferred embodiments, elements which are functionally equivalent to those described above in connection with the internally grounded feedthrough filter capacitor assembly 22 of FIGS. 2–6 will share common reference numbers in increments of 100. Thus, the D-type filter connector of FIGS. 12A–12F is referred to generally by the reference number 122, the hermetic connector of FIGS. 13 and 14A–14E is designated generally by the reference number 222, the circular quadpolar connector of FIGS. 15A–15F is designated generally by the reference number 322, and the connector shown in FIGS. 16A–16I is designated by the reference number 422.

In accordance with the invention, EMI filtered connectors 122–422 are provided which utilize one or more internally grounded feedthrough capacitors 132–432. Novel filtered connectors incorporating internally grounded feedthrough capacitors provide a number of very important advantages including:

1. The elimination of the capacitor's OD or perimeter termination;
2. Reduced cost because of elimination of the metallization and firing steps for the OD termination;
3. Greatly reduced mechanical stress because the capacitor is free to float on its pins;
4. The capacitor is much more rugged and resistant to both thermal shock and mechanical stresses due to mismatches in thermal coefficients of expansion;
5. Capacitor installation is greatly simplified;
6. Reliability is improved; and
7. The capacitor is much less subject to damage during the insertion stresses created during connector mating.

Figure 12A:
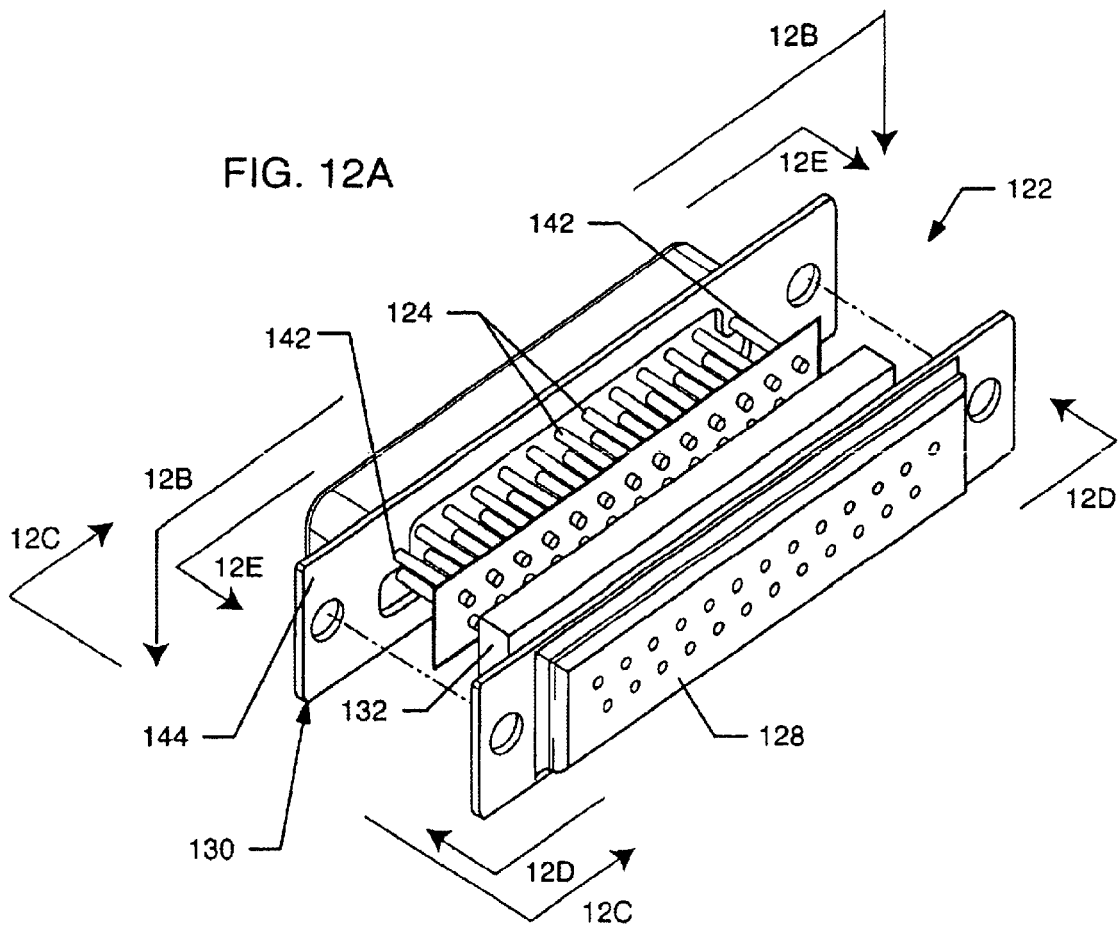
FIGS. 12A–12F illustrate a sub D-type filtered connector with twenty-five pins and utilizing an internally grounded feedthrough capacitor.
Figure 12B:
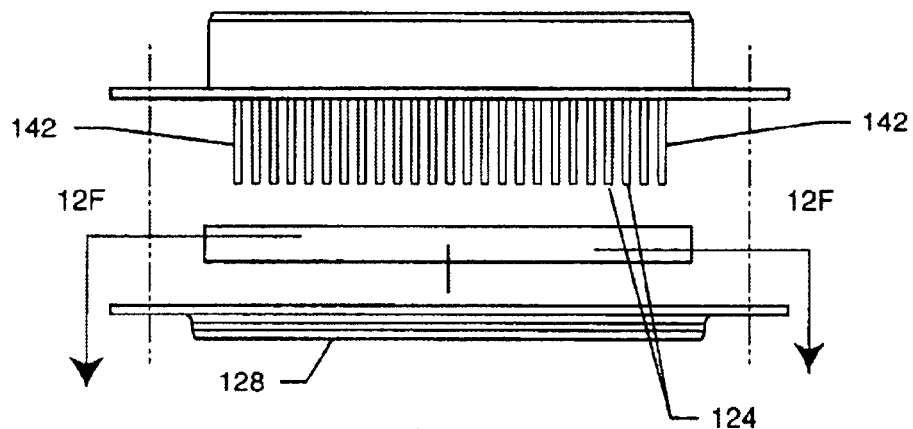
Figure 12C:
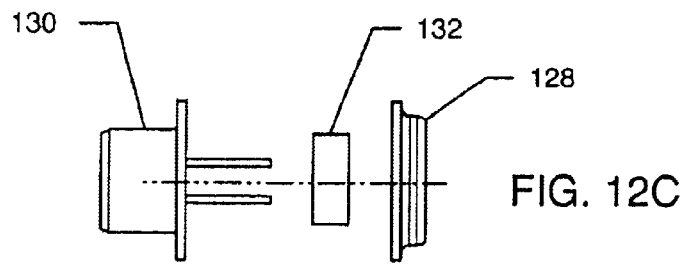
Figure 12D:
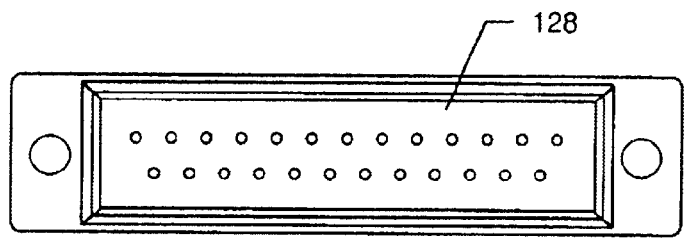
Figure 12E:
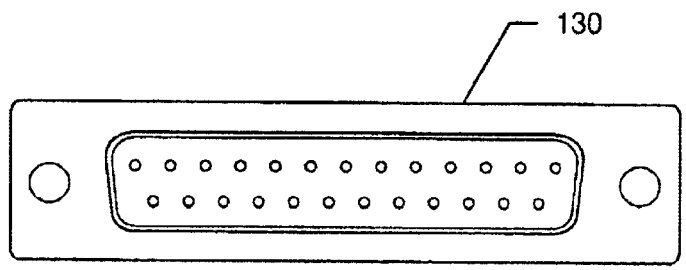
Figure 12F:
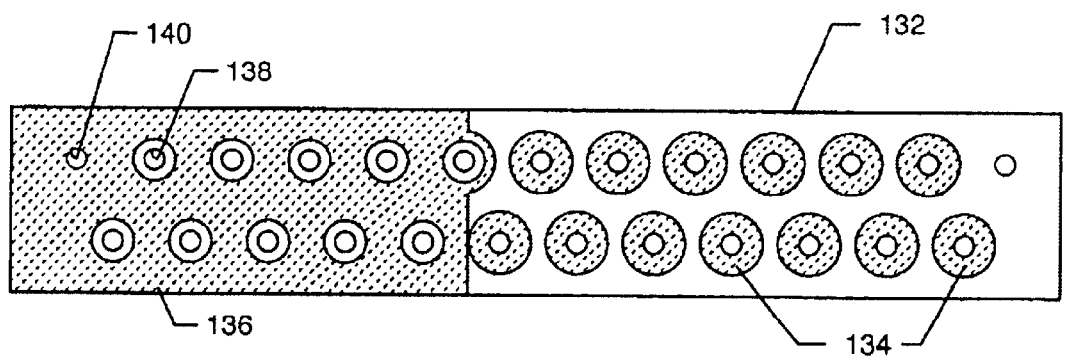

With reference to FIGS. 12A–12F, there is shown a sub D-type filtered connector 122 utilizing an internally grounded capacitor 132. A novel feature of this approach is that two of the ground pins 142 (the one furthest from the left and the one furthest from the right) are grounded right to the metallic case 144 of the connector itself (the pins may be attached by welding, brazing, soldering, conductive adhesives, swadging, press-in or the like). The capacitor feedthrough holes 138, 140 are then attached to each one of the pins 124, 142 (including the two grounded pins 142). The attachment to the ground pins 142 connects the capacitor ground electrode plate stack 136 in accordance with the principles of the internally grounded capacitor. These pin to capacitor feedthrough hole attachments can be made by automated wave soldering processes, conductive adhesives, spring contact fingers, or the like. This novel connector design method allows the capacitor 132 to float entirely on the pins 124, 142 with no mechanical connection at all between the capacitor outside perimeter and the case itself. This completely eliminates the need for capacitor outside perimeter metallization which is itself an expensive process. The active feedthrough holes 138 of the capacitor of FIG. 12 are connected to the other connector pins 124 which provides effective EMI filtering. In FIG. 12F, the ground electrode plate is cut away so that the active electrode plates are partially exposed. A plurality of ground and active electrode plate sets 136, 134 are stacked up to achieve the desired capacitance value.

Generally, the active area of each capacitor is adjusted by controlling the area of the active electrode plate (silk screen design and metal laydown control). Those pins that have a smaller active electrode area will have less capacitance. The voltage rating of the capacitor is dependant upon the dielectric thickness between the electrode plates and the width and accuracy of the capacitor margin areas. In order to manufacture such large planar array capacitors successfully, accurate registration of the active and ground electrode plates is critical. In order to accomplish this, large planar array capacitors are typically manufactured using full or modified wet stack techniques which includes automated silk screening of the electrodes. Accurate hole drilling is also critical. A significant amount of process "art" is involved in this manufacturing operation, particularly in light of the non-linear shrinkage characteristics of the large ceramic arrays wherein the hole to hole spacing may vary.

Figure 13:
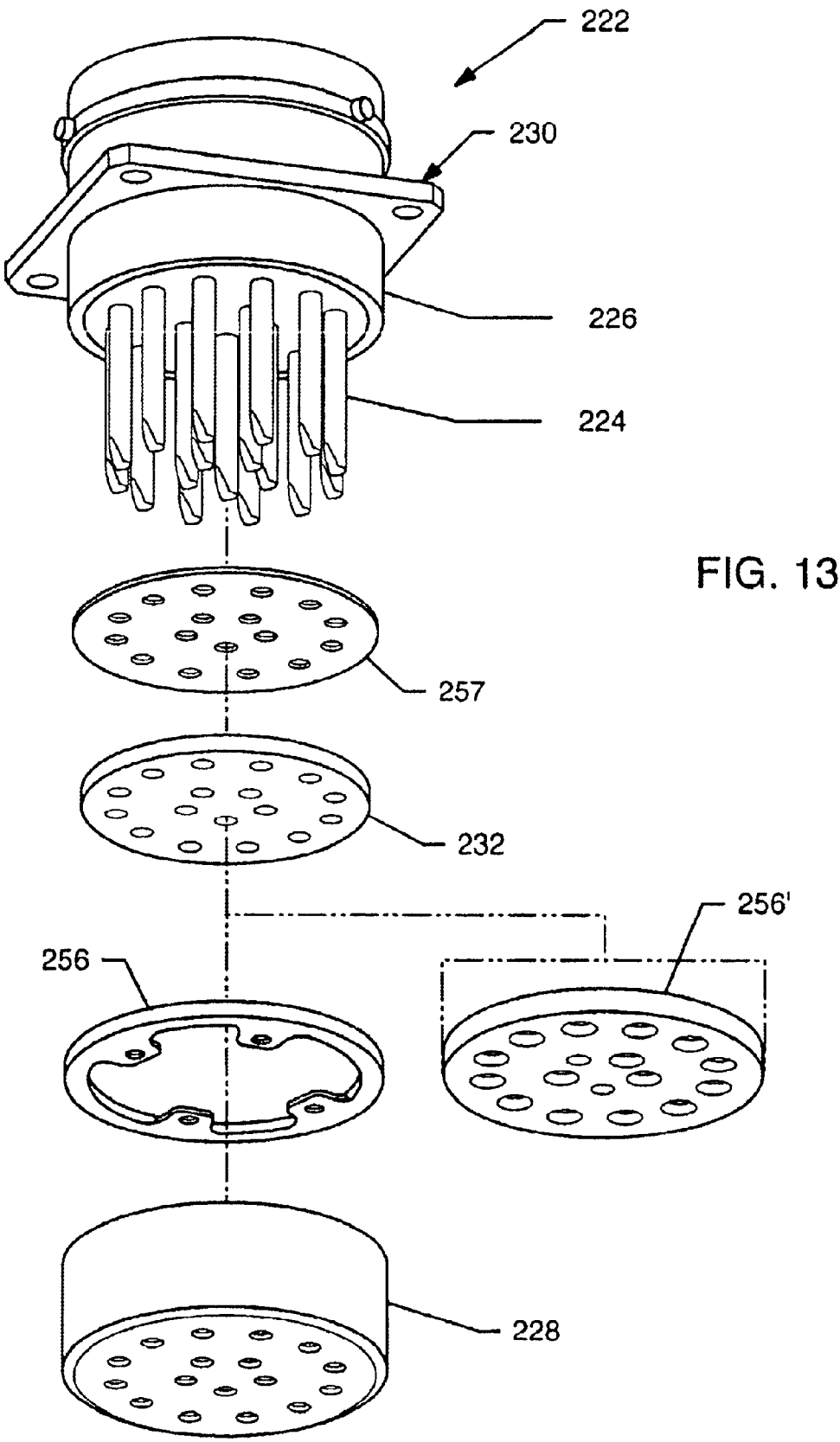
FIG. 13 shows an hermetic connector with a novel grounding ring for providing one or more grounded pins for the internally grounded capacitor.
Figure 14A:
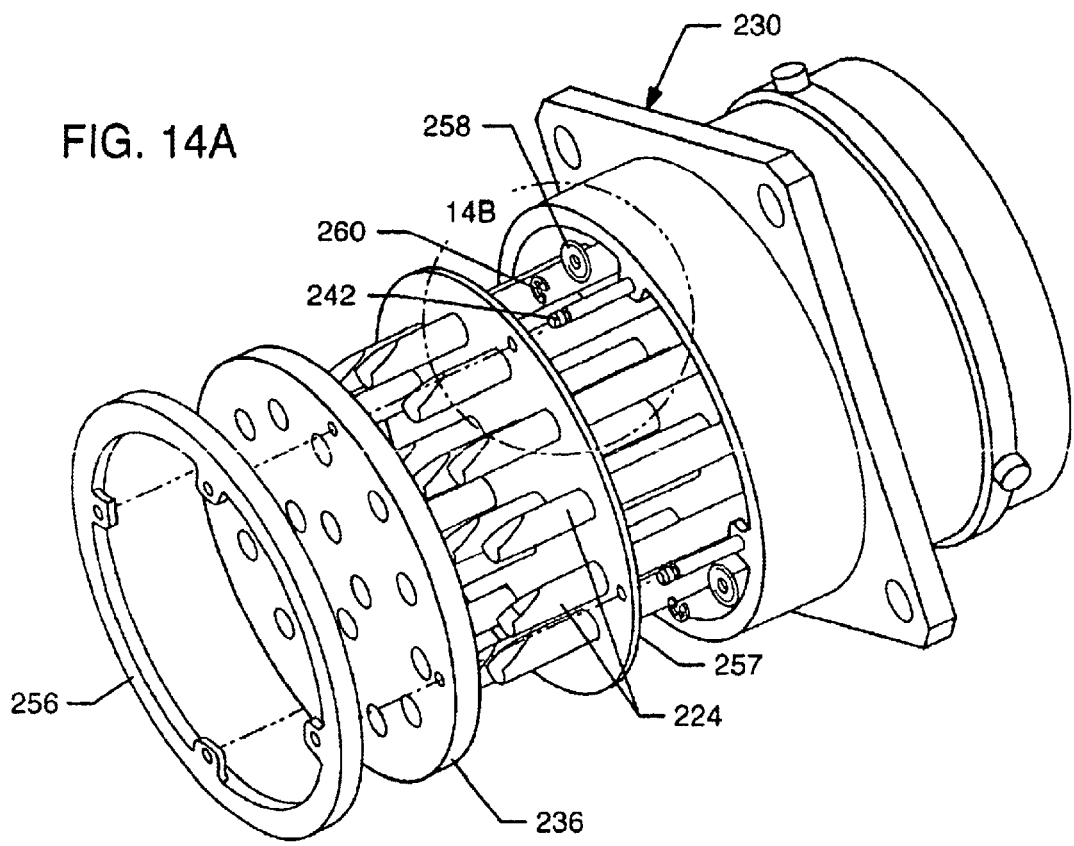
FIGS. 14A–14E show an hermetically sealed connector with internally grounded feedthrough capacitor with novel locking clips and retaining ring.
Figure 14B:
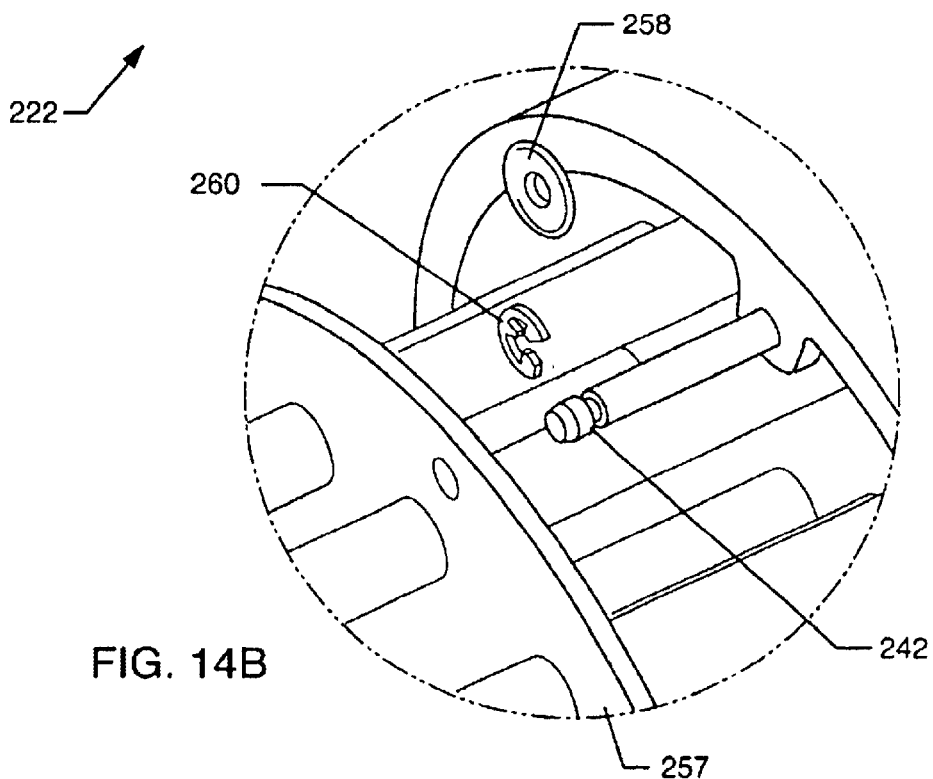
Figure 14C:
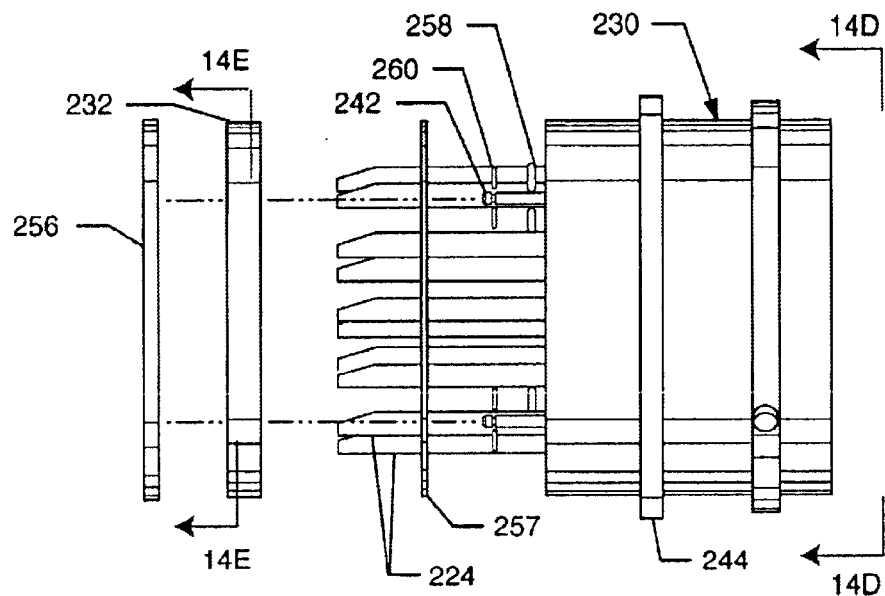
Figure 14D:
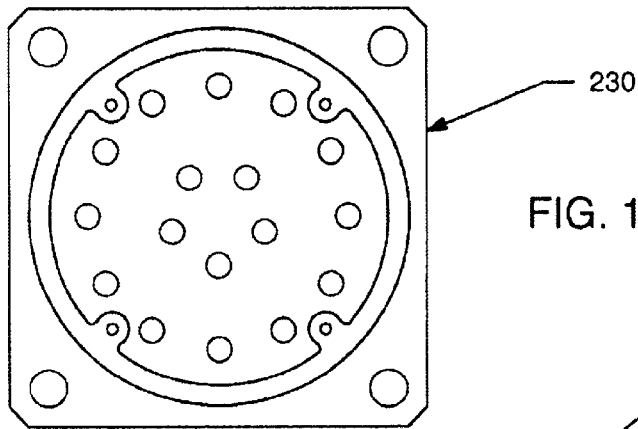
Figure 14E:
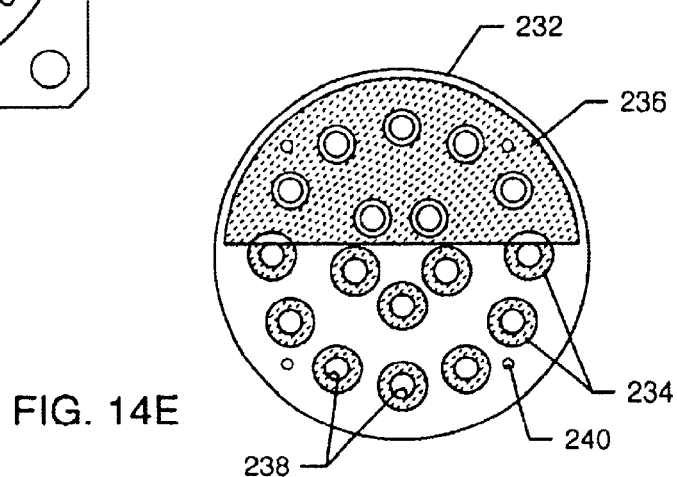
Figures 15D, 15E, 15F:
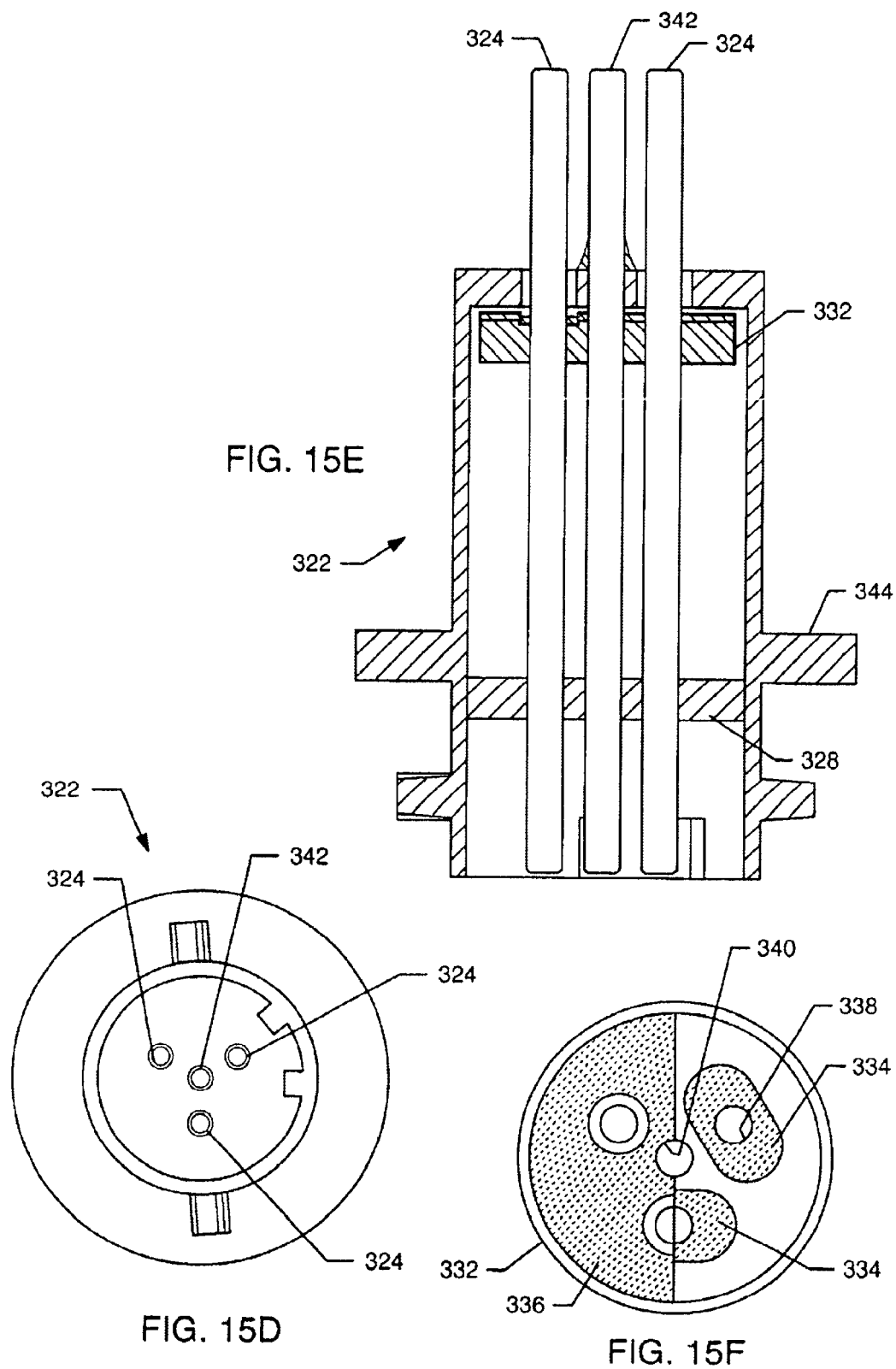
Figure 16A:
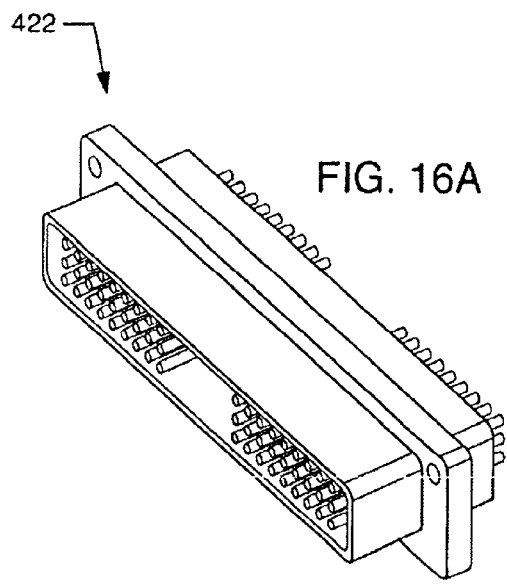
FIGS. 16A–16I illustrate how two or more individual internally grounded feedthrough capacitors can be used to provide filtering in a very large connector array or connector block.
Figure 16B:
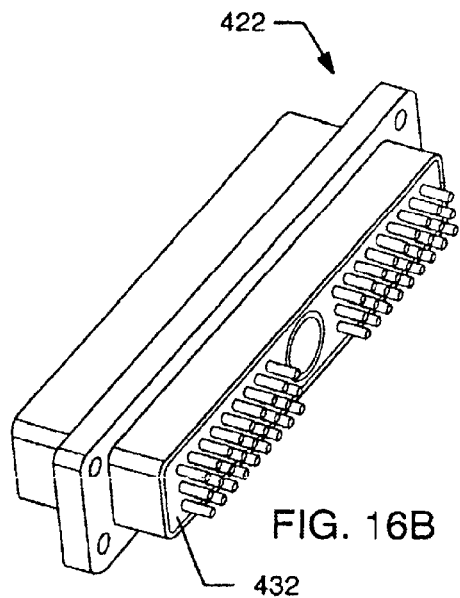
Figure 16C:
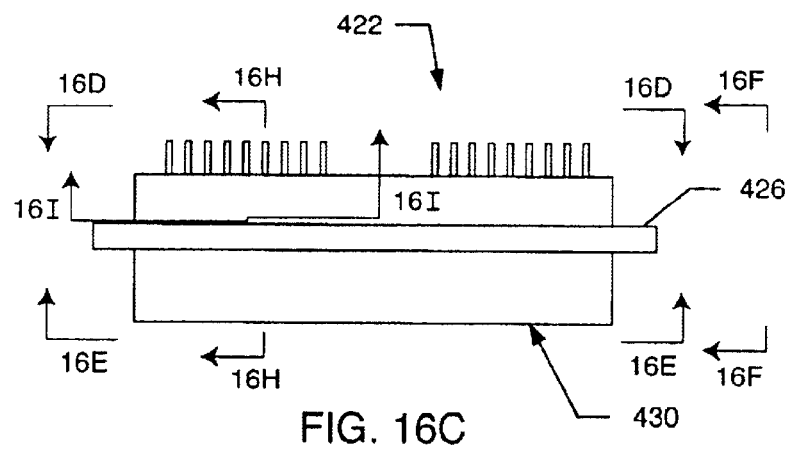
Figure 16D:
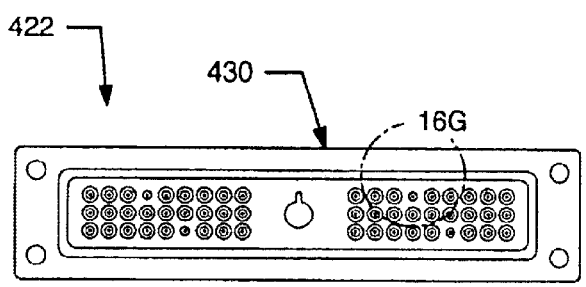
Figure 16E:
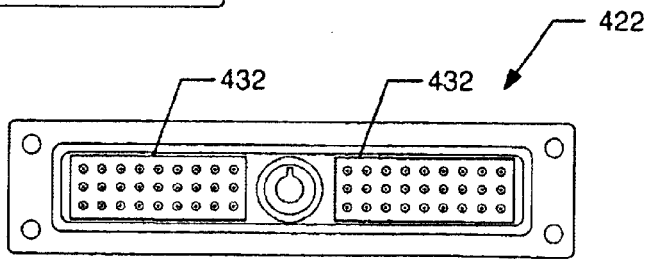
Figure 16F:
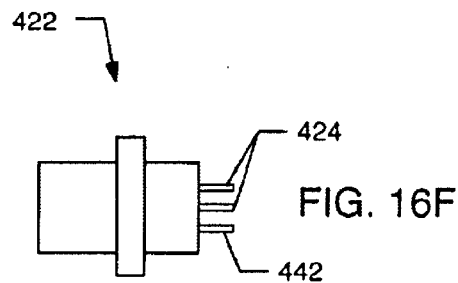
Figure 16G:
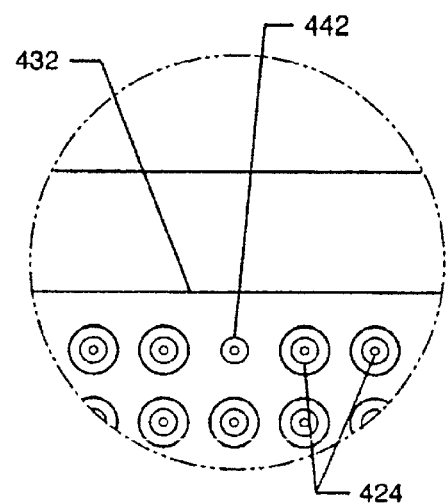
Figure 16H:
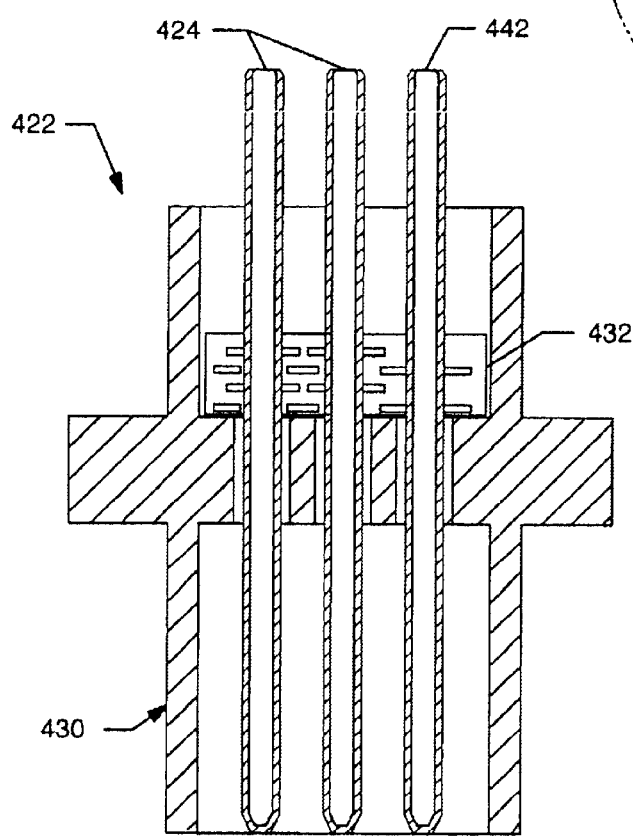
Figure 16I:
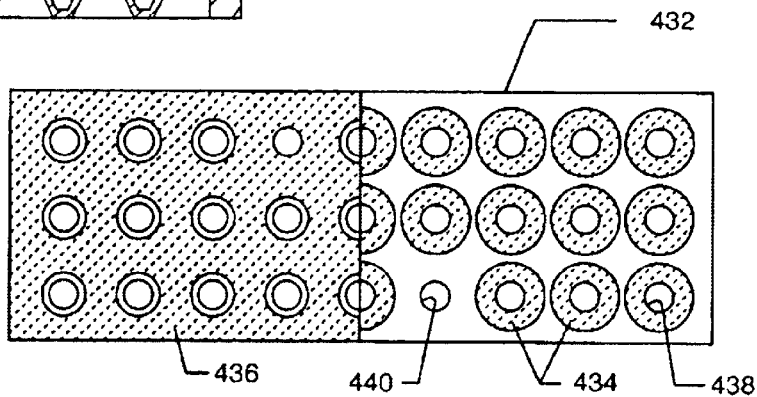

FIGS. 13 and 14A–14E illustrate a novel military-style filtered hermetic connector 222 incorporating an internally grounded feedthrough capacitor 232. In this case, a special grounding ring 256 is slipped over the connector pins 224, 242. In FIG. 13, two different grounding ring options are illustrated which shows that the designer can select any of the pins to be grounded. An attachment is made of the grounding ring 256, 256' to the connector housing 244. This attachment can be either through welding, brazing, soldering, press fit and the like. An electrical connection is also made from the grounding ring 256, 256' to two or more of the connector housing pins 242. As one can see the grounding ring 256, 256' could ground as many pins 242 as desired around the circumference of the connector housing 244. Further, an insulative washer 257 is disposed between the capacitor array 232 and the connector housing 226. In the section view of FIG. 14E, the ground electrode is partially cut away to reveal the active electrodes.

There are a number of other methods for providing grounded pins 242 for use in an internally grounded filtered connector 222. For example, the grounding ring 256 as shown in FIG. 13 could be omitted and instead the inside diameter of the connector housing 244 could be machined in such a way to ground one or more of the connector pins. FIGS. 14A–14E illustrate such a connector, which has a number of ground pins 242, which are integral to the connector housing 244.

Internally grounded feedthrough capacitors 232 can be attached in a variety of unique ways. One such way is shown in FIGS. 14A–14E wherein conductive rubber washers 258 are used along with a retaining clip 260. An alternative to the retaining clip 260 and conductive rubber washer 258 is to use a push nut which exerts a spring force against the capacitor to seat it to the ground post(s).

FIGS. 15A–15F illustrate a smaller quadpolar hermetic connector 322 wherein the pins 324 are glass sealed into the connector housing 344. There is a centered ground pin 342 which is brazed or welded and becomes an integral part of the housing. This pin 342 may also be formed during housing manufacturing or screw machine manufacturing of the pin. It is not necessary that this ground pin 342 protrude all the way through the connector. In other words, the connector could be a tripolar connector wherein the ground pin 342 is only used to connect to the ground electrode plates 336 of the feedthrough capacitor 332. In the sectional view of FIG. 15F, the ground electrode 336 is partially cut away to reveal the active electrodes.

FIGS. 16A–16I illustrate how two or more individual internally grounded feedthrough capacitors 432 can be used to provide filtering in a very large connector array or connector block 422. One or more grounded pins 442 are provided for convenient attachment to the internal ground electrode plates 436 of each feedthrough capacitor. The array that is shown in FIGS. 16A–16I uses two internally grounded feedthrough capacitors 432. It will be obvious to one experienced in the art that four, six or even more capacitors could be used depending on the number of pins and the geometry of the connector. In the section view, the ground electrode is partially cut away to reveal the active electrodes.

It is important that the number of ground pins 442 and their spacing be adjusted such that the internal inductance of the ground electrode not be too high. The grounding pin 442 does cause a small amount of inductance which appears in series with the feedthrough capacitor equivalent circuit. It is a matter of geometry and design to make sure that this inductance is small enough so that the capacitor's selfresonant frequency is always above 10 GHz. This is important for military and space applications, which typically specify attenuation up to 10 GHz. For implantable medical device applications the upper frequency is 3 GHz. This is because of the body's tendency to both reflect and absorb EMI fields above 3 GHz.

From the foregoing it will be appreciated that a novel feature of the present invention is that the internally grounded electrode plate can be grounded at multiple points (not just at its outside diameter or perimeter). This overcomes a serious deficiency in prior art filtered connectors that are physically large. In a large conventional prior art filtered connector, the pins closest to the center are a relatively long distance from the outside diameter or perimeter ground. This creates inductance which tends to reduce the filtering efficiency (attenuation in dB) of these pins. This situation is remedied with the novel internal grounded connector by the addition of a grounded pin near to the center of the array. This multipoint ground attachment assures that the capacitor ground plane will present a very low RF impedance to ground which guarantees that the feedthrough capacitor will operate as a broadband filter with a high level of attenuation.

Another novel feature of the internal ground is the elimination of the OD termination and also the elimination of the need for an electrical/mechanical connection between the shielded case or housing and the capacitor OD (or perimeter in the case of rectangular feedthrough).

A variety of alternate methods of grounding the pins for the internally grounded feedthrough capacitor(s) to be mounted in filtered connectors will be apparent to those skilled in the art. There are literally thousands of connector configurations in the market place. L, PI, T and other low pass EMI filter circuit configurations simply involve adding one or more inductors, ferrite beads, or ferrite slabs to the concepts that have been described herein. The illustrations herein are intended to demonstrate novel methods of adapting the internally grounded feedthrough capacitor to filtered connector applications but are not intended to limit the scope of the invention.

What is claimed is:

1. An EMI filtered connector, comprising:
   a plurality of conductive terminal pins;
   a grounded conductive connector housing through which the terminal pins pass in non-conductive relation;
   an array of feedthrough filter capacitors each having a distinct first set of electrode plates, a non-distinct second set of electrode plates, and a first passageway through which a respective terminal pin extends in conductive relation with the first set of electrode plates;
   at least one ground lead conductively coupled to the conductive connector housing, and extending into a second passageway through the array of feedthrough filter capacitors in conductive relation with the second set of electrode plates; and
   a grounding ring conductively coupled to the ground lead and to the connector housing.

2. The EMI filtered connector of claim 1, wherein an outer peripheral surface of the array of feedthrough filter capacitors is non-conductive.

3. The EMI filtered connector of claim 1, including an insulator disposed in or adjacent to the connector, for mounting the conductive terminal pins for passage through the conductive connector with the conductive terminal pins and the connector in non-conductive relation.

4. The EMI filtered connector of claim 1, wherein the ground lead forms a portion of the connector housing.

5. The EMI filtered connector of claim 1, wherein the array of feedthrough filter capacitors is symmetrical about the ground lead.

6. The EMI filtered connector of claim 1, wherein the array of feedthrough filter capacitors is asymmetrical about the ground lead.

7. The EMI filtered connector of claim 1, including a plurality of arrays of feedthrough filter capacitors, each having its own non-distinct second set of electrode plates.

8. The EMI filtered connector of claim 1, including a conductive washer and a retaining clip for securing the grounding ring to the ground lead.

9. The EMI filtered connector of claim 1, including a plurality of ground leads in conductive relation with the second set of electrode plates, wherein the ground leads are conductively coupled to the grounding ring.

10. The EMI filtered connector of claim 1, including an insulative washer disposed between the array of feedthrough filter capacitors and the connector housing.

11. The EMI filtered connector of claim 1, including means for hermetically sealing passage of the terminal pins through the connector housing.

12. The EMI filtered connector of claim 1, including means for hermetically sealing passage of the ground lead through the connector housing.

13. An EMI filtered connector, comprising:
    a plurality of conductive terminal pins;
    a grounded conductive connector housing through which the terminal pins pass in non-conductive relation;
    an array of feedthrough filter capacitors each having a distinct first set of electrode plates, a non-distinct second set of electrode plates, and a first passageway through which a respective terminal pin extends in conductive relation with the first set of electrode plates, the outer peripheral surface of the array of feedthrough filter capacitors being non-conductive;
    at least one ground lead conductively coupled to the conductive connector housing, and extending into a second passageway through the array of feedthrough filter capacitors in conductive relation with the second set of electrode plates;
    a grounding ring conductively coupled to the ground lead and to the connector housing; and
    an insulator disposed in or adjacent to the connector, for mounting the conductive terminal pins for passage through the conductive connector with the conductive terminal pins and the connector in non-conductive relation.

14. The EMI filtered connector of claim 13, including means for hermetically sealing passage of the terminal pins through the connector housing, and means for hermetically sealing passage of the ground lead through the connector housing.

15. The EMI filtered connector of claim 13, wherein the ground lead forms a portion of the connector housing.

16. The EMI filtered connector of claim 13, wherein the array of feedthrough filter capacitors is symmetrical about the ground lead.

17. The EMI filtered connector of claim 13, wherein the array of feedthrough filter capacitors is asymmetrical about the ground lead.

18. The EMI filtered connector of claim 13, including a plurality of arrays of feedthrough filter capacitors, each having its own non-distinct second set of electrode plates.

19. The EMI filtered connector of claim 13, including a conductive washer and a retaining clip for securing the grounding ring to the ground lead.

20. The EMI filtered connector of claim 13, including a plurality of ground leads in conductive relation with the second set of electrode plates, wherein the ground leads are conductively coupled to the grounding ring.

21. The EMI filtered connector of claim 13, including an insulative washer disposed between the array of feedthrough filter capacitors and the connector housing.

22. An EMI filtered connector, comprising:

a plurality of conductive terminal pins;

a grounded conductive connector housing through which the terminal pins pass in non-conductive relation;

an array of feedthrough filter capacitors each having a distinct first set of electrode plates, a non-distinct second set of electrode plates, and a first passageway through which a respective terminal pin extends in conductive relation with the first set of electrode plates, the outer peripheral surface of the array of feedthrough filter capacitors being non-conductive;

a plurality of ground leads forming a portion of the connector housing and extending into second passageways through the array of feedthrough filter capacitors in conductive relation with the second set of electrode plates;

an insulator disposed in or adjacent to the connector, for mounting the conductive terminal pins for passage through the conductive connector with the conductive terminal pins and the connector in non-conductive relation; and a grounding ring conductively coupled to the ground leads and to the connector housing, and a connective washer and a retaining clip for securing the grounding ring to the ground leads, wherein the ground leads are all conductively coupled to the grounding ring.

23. The EMI filtered connector of claim 22, wherein the array of feedthrough filter capacitors is asymmetrical about the ground lead.

24. The EMI filtered connector of claim 22, including a plurality of arrays of feedthrough filter capacitors, each having its own non-distinct second set of electrode plates.

25. The EMI filtered connector of claim 22, wherein the array of feedthrough filter capacitors is symmetrical about the ground lead.

* * * * *